United States Patent
Bertrand et al.

(10) Patent No.: US 8,680,274 B2
(45) Date of Patent: Mar. 25, 2014

(54) BENT ALLENES, AND THEIR METAL COMPLEXES

(75) Inventors: Guy Bertrand, Riverside, CA (US); Vincent Lavallo, Riverside, CA (US); Adam C. Dyker, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 343 days.

(21) Appl. No.: 12/812,423

(22) PCT Filed: Jan. 9, 2009

(86) PCT No.: PCT/US2009/030647
§ 371 (c)(1),
(2), (4) Date: Oct. 8, 2010

(87) PCT Pub. No.: WO2009/089483
PCT Pub. Date: Jul. 16, 2009

(65) Prior Publication Data
US 2011/0021775 A1    Jan. 27, 2011

Related U.S. Application Data

(60) Provisional application No. 61/020,309, filed on Jan. 10, 2008.

(51) Int. Cl.
*C07F 15/00* (2006.01)
*C07D 231/10* (2006.01)
*C07D 403/06* (2006.01)
*C07F 11/00* (2006.01)
*C07D 235/20* (2006.01)

(52) U.S. Cl.
USPC .......... 546/4; 548/103; 548/305.7; 548/364.1

(58) Field of Classification Search
USPC ................... 546/4; 548/103, 305.7, 364.1
See application file for complete search history.

(56) References Cited

U.S. PATENT DOCUMENTS

| | | | |
|---|---|---|---|
| 4,045,221 A | 8/1977 | Dominh | |
| 6,642,401 B2 * | 11/2003 | Watanabe et al. | 556/12 |
| 6,686,428 B2 | 2/2004 | Zhang et al. | |
| 6,818,586 B2 | 11/2004 | Grubbs et al. | |

OTHER PUBLICATIONS

Wojcicki "Allenyls and propargyls: versatile ligands in transition-metal chemistry" Inorganic Chemistry Communications, 2002, vol. 5, pp. 82-97.*

International Search Report mailed on Mar. 18, 2009, for International Application No. PCT/US09/30647 filed on Jan. 9, 2009, 3 pages.

Wojcicki, A., "Allenyls and propargyls: versatile ligands in transition-metal chemistry," *Inorganic Chemistry Communications*, 2002, vol. 5, pp. 82-97.

* cited by examiner

*Primary Examiner* — Joseph Kosack
(74) *Attorney, Agent, or Firm* — Kilpatrick Townsend & Stockton LLP; William B. Kezer

(57) ABSTRACT

Stable, bent allenes, organometallic complexes of bent allenes are provided along with methods of conducting chemical processes such as olefin metathesis, comprising contacting an olefin substrate with an organometallic complex as described herein, under suitable conditions.

24 Claims, 7 Drawing Sheets

ORTEP view of one of the enantiomers of 2a·2THF (for clarity, H atoms are omitted).

ORTEP view of one of the enantiomers of 6 (for clarity, H atoms are omitted).

ORTEP view of one of the enantiomers of 8 (for clarity, H atoms are omitted).

BENT ALLENES, AND THEIR METAL COMPLEXES

STATEMENT AS TO RIGHTS TO INVENTIONS MADE UNDER FEDERALLY SPONSORED RESEARCH AND DEVELOPMENT

This invention was made with the support of the University of California, Riverside CNRS UCR/CNRS Agreement and NSF CHE 0518675.

CROSS-REFERENCES TO RELATED APPLICATIONS

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Carbon-carbon multiple bonding is so well understood that ethene, acetylene, and allene (1,2-propadiene) derivatives are the benchmarks for comparisons with the analogues involving multiple bonding between the heavier main group elements (W. Kutzelnigg, *Angew. Chem. Int. Ed. Engl.* 23, 272-295 (1984), E. Rivard, P. P. Power, *Inorg. Chem.* 46, 10047-10064 (2007), P. P. Power *Chem. Rev.* 99, 3463-3503 (1999)). In line with hybridization theory, allenes $A_1$ (see FIG. 1) have a linear CCC skeleton with orthogonal pairs of substituents (N. Krause, A. S. K. Hashmi, Eds., *Modern Allene Chemistry* (Wiley-VCH: Weinheim, 2004)). The allene framework is so rigid that even minor deviations from linearity are of note. In a paper from 1995, entitled "A remarkably bent allene. X-ray crystal structure and ab initio calculations", Weber et al. (E. Weber, W. Seichter, B. Hess, G. Will, H. J. Dasting, *J. Phys. Org. Chem.* 8, 94-96 (1995)) described compound $A_2$, which is still today the most severely bent acyclic allene, with a CCC bond angle of 170.1°. The authors demonstrated that the non-linearity was due to packing effects in the crystal. To significantly bend an allene, it is necessary to constrain the C=C=C π-system into a ring, but limitations rapidly emerge. Even the low temperature NMR characterization of cyclic allenes is limited to those containing more than seven carbon atoms (M. Christi, in *Modern Allene Chemistry*, N. Krause, A. S. K. Hashmi, Eds., (Wiley-VCH: Weinheim, 2004), pp 243-357; the only exception is the 1,2,4,6-cycloheptatetraene $A_3$, incarcerated in a molecular container by Warmuth (R. Warmuth, M. A. Marvel, *Chem. Eur. J.* 7, 1209-1220 (2001). The kinetically protected 1,2-cyclooctadiene $A_4$ (calculated CCC angle: 158°) (J. D. Price, R. P. Johnson, *Tetrahedron. Lett.* 39, 4679-4682 (1986), and the trisilicon (Y. Pang, S. A. Petrich, V. G. Young Jr., M. S. Gordon, T. J. Barton, *J. Am. Chem. Soc.* 115, 2534-2536 (1993), T. Shimizu, F. Hojo, W. Ando, *J. Am. Chem. Soc.* 115, 3111-3115 (1993)) and diphosphorus (M. A. Hofman, U. Bergstrasser, G. J. Reiss, L. Nyulaszi, M. Regitz, *Angew. Chem. Int. Ed.* 39, 1261-1263 (2000)) containing six-membered rings $A_{5-7}$ (crystallographically observed CCC angles: 166, 161 and 156°, respectively) are the smallest ring allenes isolated. Note that because of the presence of the heavier main group elements, the allene fragment of $A_{5-7}$ is not significantly more distorted than in the eight-membered ring $A_4$. Smaller ring allenes $A_8$ are only known as reaction intermediates, in line with calculations that indicate a strong diradical character $A_8'$ (K. J. Daoust, S. M. Hernandez, K. M. Konrad, I. D. Mackie, J. Winstanley, R. P. Johnson, *J. Org. Chem.* 71, 5708-5714 (2006).

In marked contrast with all-carbon allene fragments (C=C=C), crystallographic (S. Ishida, T. Iwamoto, C. Kabuto, M. Kira, *Nature* 421, 725-727 (2003), T. Iwamoto, H. Masuda, C. Kabuto, M. Kira, *Organometallics* 24, 197-199 (2005)) and computational studies (M. Rosa, M. Karni, Y. Apeloig, *J. Am. Chem. Soc.* 126, 10544-10545 (2004), M. Kosa, M. Karni, Y. Apeloig, *J. Chem. Theory Comput.* 2, 956-964 (2006), B. Pinter, A. Olasz, K. Petrov, T. Veszpremi, *Organometallics* 26, 3677-3683 (2007)) have shown that allenes based on heavier group 14 elements (E=E=E; E: Si, Ge) ($B_{1-2}$) are highly flexible, and exhibit a bent structure (136.5° and 122.6°, respectively) even without being confined to a ring. The striking differences in the geometry between all carbon allenes A and their heavier element congeners B is mainly due to the "first long row anomaly", as described by Grützmacher (H. Grützmacher, *Science* 289, 737-738 (2000)). The first long row elements tend to form hybrids from s and p orbitals that lead to the familiar linear, trigonal and tetragonal bonding geometries of carbon. Second long row elements largely avoid hybridization (W. Kutzelnigg, *Angew. Chem. Int. Ed. Engl.* 23, 272-295 (1984)). Among the consequences, second and higher row elements are generally reluctant to form multiple bonds, and therefore heavier element-heavier element π-bonds are weak (W. Kutzelnigg, *Angew. Chem. Int. Ed. Engl.* 23, 272-295 (1984), E. Rivard, P. P. Power, *Inorg. Chem.* 46, 10047-10064 (2007), P. P. Power *Chem. Rev.* 99, 3463-3503 (1999)).

Making an analogy with the heavier main group element allenes B, we reasoned that weakening the π-bonds of all-carbon allenes A should impart a greater flexibility to the CCC skeleton, and therefore allow for the preparation of stable small ring allenes.

BRIEF SUMMARY OF THE INVENTION

The present invention provides stable, bent allenes, organometallic complexes of bent allenes and methods of conducting chemical processes such as olefin metathesis, comprising contacting an olefin substrate with an organometallic complex as described herein, under metathesis conditions.

In one aspect, the present invention provides an organometallic complex comprising a metal atom selected from groups 1-16 of the periodic table and a C—C—C bent allene two- to four-electron-donating ligand. In one group of embodiments, the C—C—C bent allene two- to four-electron-donating ligand has the formula:

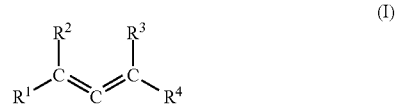

(I)

wherein each of $R^1$, $R^2$, $R^3$ and $R^4$ is independently selected from the group consisting of amino, aryl, heteroaryl, $C_{1-10}$ alkoxy, $C_{2-10}$ alkenyloxy, $C_{2-10}$ alkynyloxy, $C_{1-10}$ alkyl, $C_{3-10}$ cycloalkyl, $C_{2-10}$ alkenyl, $C_{3-10}$ cycloalkenyl, $C_{2-10}$ alkynyl, halogen, aryloxy, heteroaryloxy, $C_{2-10}$ alkoxycarbonyl, $C_{1-10}$ alkylthio, $C_{2-10}$ alkenylthio, $C_{2-10}$ alkynylthio, $C_{1-10}$ alkylsulfonyl, $C_{1-10}$ alkylsulfinyl, aryl-$C_{1-10}$ alkyl, heteroaryl-$C_{1-10}$ alkyl, aryl-$C_{1-10}$ heteroalkyl, heteroaryl-$C_{1-10}$ heteroalkyl, a phosphorus group, a silicon group and a boron group;

wherein optionally two or four of $R^1$, $R^2$, $R^3$ and $R^4$ are combined to form a 5- to 8-membered carbocyclic or heterocyclic ring; wherein the aliphatic or aromatic portions of $R^1$, $R^2$, $R^3$ and $R^4$ are optionally substituted with from 1 to 4 substituents selected from the group consisting of halogen, cyano, nitro, $C_{1-4}$ alkyl, $C_{2-6}$ alkenyl, $C_{2-6}$ alkynyl, aryl, $C_{1-6}$ alkoxy, $C_{2-6}$ alkenyloxy, $C_{2-6}$ alkynyloxy, aryloxy, $C_{2-6}$ alkoxycarbonyl, $C_{1-6}$ alkylthio, $C_{1-6}$ alkylsulfonyl, $C_{1-6}$ alkylsulfinyl, oxo, imino, thiono, primary amino, carboxyl, $C_{1-6}$ alkylamino, $C_{1-6}$ dialkylamino, amido, nitrogen heterocycles, hydroxy, thiol and phosphorus groups; wherein at least one atom directly adjacent to an allene carbon is selected from the group consisting of N, P, O and S In a related group of embodiments, the C—C—C bent allene two- to four-electron-donating ligand has the formula:

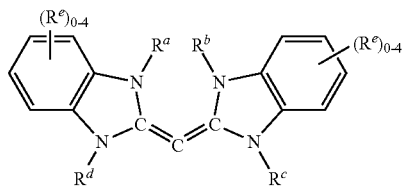

wherein each of $R^a$, $R^b$, $R^c$ and $R^d$ are independently selected from the group consisting of hydrogen, $C_{1-10}$ alkyl, $C_{3-10}$ cycloalkyl, $C_{2-10}$ alkenyl, $C_{3-10}$ cycloalkenyl, $C_{2-10}$ alkynyl, $C_{2-10}$ alkoxycarbonyl, $C_{1-10}$ alkylsulfonyl, $C_{1-10}$ alkylsulfinyl, aryl-$C_{1-4}$ alkyl and heteroaryl-$C_{1-4}$ alkyl; and each $R^e$ is a substituent independently selected from the group consisting of halogen, cyano, nitro, $C_{1-4}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{2-6}$ alkoxycarbonyl, $C_{1-6}$ alkylthio, $C_{1-6}$ alkylsulfonyl, $C_{1-6}$ alkylsulfinyl, primary amino, carboxyl, $C_{1-6}$ alkylamino, $C_{1-6}$ dialkylamino, amido, hydroxy and thiol groups.

In another related group of embodiments, the C—C—C bent allene two- to four-electron-donating ligand has the formula:

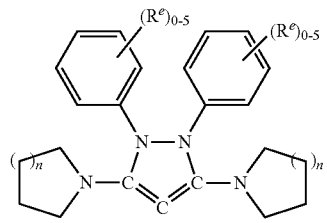

wherein the subscripts n are each independently an integer of from 0 to 4; and each $R^e$ is a substituent independently selected from the group consisting of halogen, cyano, nitro, $C_{1-4}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{2-6}$ alkoxycarbonyl, $C_{1-6}$ alkylthio, $C_{1-6}$ alkylsulfonyl, $C_{1-6}$ alkylsulfinyl, primary amino, carboxyl, $C_{1-6}$ alkylamino, $C_{1-6}$ dialkylamino, amido, hydroxy and thiol groups.

In another aspect, the present invention provides reaction mixtures comprising an organometallic complex as described above and herein, a solvent and an olefin substrate, wherein the olefin substrate is selected to participate in an olefin metathesis reaction.

In yet another aspect, the present invention provides methods for conducting olefin metathesis, comprising contacting an olefin substrate with an organometallic complex as described above and herein, under metathesis conditions.

In still another aspect, the present invention provides methods for conducting carbon-carbon coupling reactions, carbon-heteroatom coupling reaction and 1,2-additions to multiple bonds, comprising contacting suitable substrates or reactants in the presence of an organometallic complex as described above and herein, under conditions appropriate for the desired reaction.

DETAILED DESCRIPTION OF THE INVENTION

Abbreviations and Definitions

Figure 1:
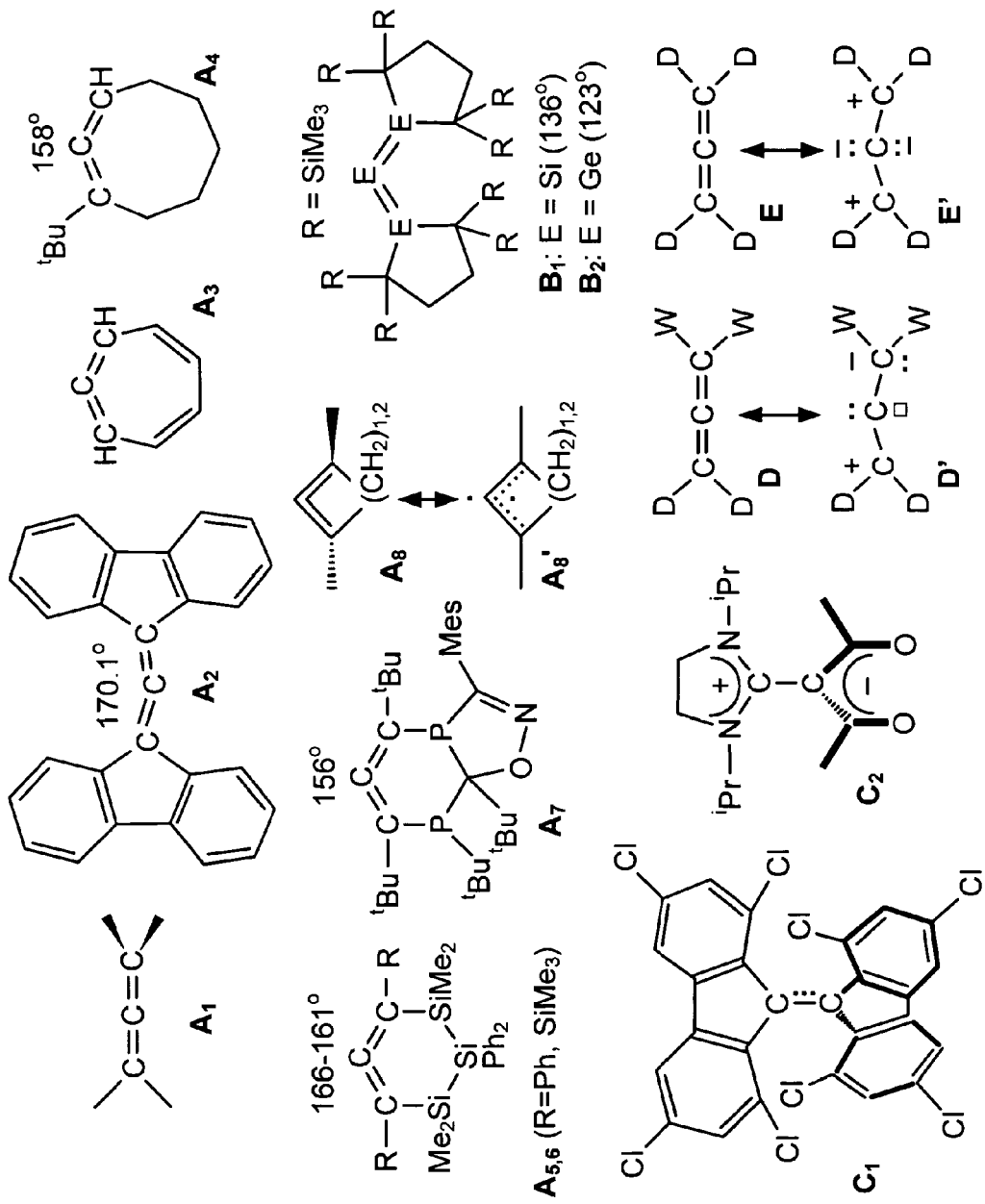
FIG. 1 provides the structures of components $A_1$ through $A_8$, $B_1$, $B_2$, $C_1$, $C_2$, D, D', E and E' as discussed in the Background.

Abbreviations used herein have their common and accepted meanings to one of skill in the art. Examples of the abbreviations are t-Bu, tertiary butyl; Me, methyl; THF, tetrahydrofuran.

In the present description the term "alkyl", alone or in combination, refers to a straight-chain or branched-chain alkyl group having the indicated number of carbon atoms. For example, $C_{1-10}$alkyl refers to an alkyl group having from one to ten carbon atoms with the remaining valences occupied by hydrogen atoms. Preferred alkyl groups are those with 1 to 8 carbon atoms, more preferably a straight or branched-chain alkyl group with 1 to 6 carbon atoms and particularly preferred are straight or branched-chain alkyl groups with 1 to 4 carbon atoms. Examples of straight-chain and branched $C_{1-10}$ alkyl groups are methyl, ethyl, propyl, isopropyl, butyl, isobutyl, tent-butyl, the isomeric pentyls, the isomeric hexyls, the isomeric heptyls and the like.

The term "cycloalkyl", alone or in combination, refers to a cyclic alkyl group having 3 to 8 carbon atoms as ring vertices. Preferred cycloalkyl groups are those having 3 to 6 carbon atoms. Examples of $C_{3-8}$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl.

The term "cycloalkenyl", alone or in combination, refers to a cyclic alkenyl group having 3 to 8 carbon atoms as ring vertices. Preferred cycloalkyl groups are those having 3 to 6 carbon atoms. Examples of $C_{3-8}$ cycloalkyl are cyclopropenyl, cyclopentenyl dimethylcyclopropenyl and cyclobutyl.

The term "alkoxy", alone or in combination, signifies a group of the formula alkyl-O— in which the term "alkyl" has the previously given definition. Examples of alkoxy group include methoxy, ethoxy, n-propoxy, iso-propoxy, n-butoxy, iso-butoxy, sec-butoxy and tert-butoxy. Preferred alkoxy groups are methoxy and ethoxy.

The term "alkenyl", alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl", alone or in combination refers to a straight-chain or branched hydrocarbon residue having a carbon carbon triple bond and the indicated number of carbon atoms. Preferred alkynyl groups have up to 8, preferably up to 6, particularly preferred up to 4 carbon atoms. Examples of alkynyl groups are ethynyl, 1-propynyl, 1-butynyl and 2-butynyl The terms "alkylthio," "alkylsulfonyl," "alkylsulfinyl" and "arylsulfonyl" refer to groups having the formula —S—$R^i$—S(O)$_2$—$R^i$, —S(O)—$R^i$ and —S(O)$_2R^j$, respectively, in which $R^i$ is an alkyl group as previously defined and $R^j$ is an aryl group as previously defined.

The terms "alkenyloxy" and "alkynyloxy" refer to groups having the formula —O—$R^i$ in which $R^i$ is an alkenyl or alkynyl group, respectively.

The terms "alkenylthio" and "alkynylthio" refer to groups having the formula —S—$R^k$ in which $R^k$ is an alkenyl or alkynyl group, respectively.

The term "alkoxycarbonyl" refers to a group having the formula —C(O)O—$R^i$, wherein $R^i$ is an alkyl group as defined above and wherein the total number of carbon atoms refers to the combined alkyl and carbonyl moieties.

The term "aryl" means, unless otherwise stated, a polyunsaturated, typically aromatic, hydrocarbon group which can be a single ring or multiple rings (up to three rings) which are fused together or linked covalently, and which optionally carries one or more substituents, for example, such as halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro and the like. Non-limiting examples of unsubstituted aryl groups include phenyl, naphthyl and biphenyl. Examples of substituted aryl groups include, but are not limited to, phenyl, chlorophenyl, trifluoromethylphenyl, chlorofluorophenyl and aminophenyl.

The term "heteroalkyl," by itself or in combination with another term, means, unless otherwise stated, a stable straight or branched chain, or combinations thereof, consisting of the stated number of carbon atoms and from one to five heteroatoms, more preferably from one to three heteroatoms, selected from the group consisting of O, N, Si and S, and wherein the nitrogen and sulfur atoms may optionally be oxidized and the nitrogen heteroatom may optionally be quaternized. The heteroalkyl group is attached to the remainder of the molecule through a carbon atom or a heteroatom.

The term "heterocycloalkyl" by itself or in combination with another term refers to a cyclic hydrocarbon radical or a combination of a cyclic hydrocarbon radical with a straight or branched chain alkyl group, consisting of the stated number of carbon atoms and from one to three heteroatoms as ring members selected from the group consisting of O, N, Si and S, and wherein the nitrogen and sulfur atoms may optionally be oxidized and the nitrogen heteroatom may optionally be quaternized. The heterocycloalkyl group is attached to the remainder of the molecule through a carbon atom or a heteroatom.

The term "heteroaryl", alone or in combination, unless otherwise stated, signifies aromatic 5- to 10-membered heterocycle which contains one or more, preferably one or two hetero atoms selected from nitrogen, oxygen and sulfur, wherein nitrogen or oxygen are preferred. If desired, it can be substituted on one or more carbon atoms substituents such as halogen, alkyl, alkoxy, cyano, haloalkyl, preferably trifluoromethyl, and heterocyclyl, preferably morpholinyl or pyrrolidinyl, and the like. Examples of heteroaryls include, but are not limited to, pyridinyl or furanyl.

The term "heterocycle," alone or in combination, unless otherwise stated, refers to heteroaryl and heterocycloalkyl groups.

The term "aryloxy" and "heteroaryloxy", alone or in combination, signifies a group of the formula aryl-O— and heteroaryl-O—, respectively, in which the terms "aryl" and "heteroaryl" have the significance as provided above, such as phenyloxy, and pyridyloxy, and the like.

The term "amino", alone or in combination, signifies a primary, secondary or tertiary amino group bonded to the remainder of the molecule via the nitrogen atom, with the secondary amino group carrying an alkyl, cycloalkyl, alkenyl, cycloalkenyl, alkynyl, heteroalkyl, heterocycloalkyl, aryl or heteroaryl substituent and the tertiary amino group carrying two similar or different alkyl, cycloalkyl, alkenyl, cycloalkenyl, alkynyl, heteroalkyl, heterocycloalkyl, aryl or heteroaryl substituents. Alternatively, the two nitrogen substitutents on the tertiary amino group can be taken together to form a 3 to 7 membered ring possibly having to an additional 1 to 2 heteroatoms selected from N, O, P and S as ring vertices. Examples of amino groups include, but are not limited to, —NH$_2$, methylamino, ethylamino, phenylamino, N-phenyl-N-methoxyamino, dimethylamino, diethylamino, methyl-ethylamino, pyrrolidin-1-yl or piperidino etc., preferably amino, dimethylamino and diethylamino.

The term "alkylamino," is used in its conventional sense, and refer to a secondary amino group with an alkyl substituent, and is attached to the remainder of the molecule via the nitrogen atom of the secondary amino group. Additionally, for dialkylamino groups, the alkyl portions can be the same or different and can also be combined to form a 3-7 membered ring with the nitrogen atom to which each is attached. Accordingly, a dialkylamino group is meant to include piperidinyl, pyrrolidinyl, morpholinyl, azetidinyl and the like.

The terms "alkoxy," and "alkylthio" (or thioalkoxy) are used in their conventional sense, and refer to those alkyl groups attached to the remainder of the molecule via an oxygen atom, or a sulfur atom, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$haloalkyl" is meant to include trifluoromethyl, 2,2,2-trifluoroethyl, 4-chlorobutyl, 3-bromopropyl, and the like.

The term "amido" refers to the group —C(O)NR$^a$R$^b$ or —NR$^a$C(O)R$^b$, wherein the R$^a$ and R$^b$ substituents are independently hydrogen, alkyl, alkenyl or aryl.

The term "boron group" as used herein, refers to the group having the general formula —BR$^c$R$^d$R$^e$, wherein R$^c$, R$^d$, and R$^e$ are each an alkyl or aryl group.

The term "silicon group" as used herein, refers to the group having the general formula —SiR$^f$R$^g$R$^h$, where R$^f$, R$^g$, and R$^h$ are independently an H, an alkyl group, an alkenyl group, an alkynyl group, an aryl group, or a combination of such groups.

The term "phosphorus group" as used herein, refers to an organic phosphorus group, such as for example, phosphine, phosphinite, phosphate, phosphonate, phosphate, phosphine oxide, and phosphinate, among others.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms. Similarly, "alkenylene" and "alkynylene" refer to the unsaturated forms of "alkylene" having double or triple bonds, respectively.

The term "heteroalkylene," by itself or in combination with another term, means, unless otherwise stated, a stable branched or straight chain divalent radical derived from an heteroalkane and consisting of the stated number of carbon atoms and from one to five heteroatoms selected from the group consisting of O, N, Si and S, and wherein the nitrogen and sulfur atoms may optionally be oxidized and the nitrogen heteroatom may optionally be quaternized. Examples of heteroalkylene groups include —CH$_2$CH$_2$OCH$_2$CH$_2$OCH$_2$CH$_2$O—, —CH$_2$CH$_2$NHCH$_2$CH$_2$—, and the like.

The term "arylene" or "heteroarylene," by itself or in combination with another term means, unless otherwise stated, a divalent radical derived from a $C_{6-14}$ aromatic or $C_{5-13}$ heteroaromatic ring system that is optionally substituted with 1 to 2 $C_{1-6}$ alkyl or $C_{1-6}$ heteroalkyl groups. The arylene or heteroarylene group can be covalently attached to another molecule directly through a carbon atom on the aromatic or heteroaromatic ring, or can be covalently attached to another molecule through a carbon atom or heteroatom (if present) on the $C_{1-6}$ alkyl or $C_{1-6}$ heteroalkyl substituents on the aromatic or heteroaromatic ring.

General

The present invention resides in the discovery that stable bent allenes (see FIG. 1) can be prepared and are strong two to four electron donors in complexes with transition metals. These complexes can be useful in a variety of chemical processes, particularly olefin metathesis reactions, carbon-carbon coupling reactions, carbon-heteroatom coupling reactions, and 1,2-additions to multiple bonds.

In the present invention, the synthesis and single crystal X-ray diffraction study of a five-membered cyclic allene-lithium salt adduct is provided. Surprisingly, these all-carbon allenes can be forced to adopt a highly bent structure, even in the absence of a confining ring, as demonstrated by the isolation of a salt free acyclic derivative featuring a CCC bond angle of 134.8°. Moreover, these bent allenes behave as strong η$^1$-donor ligands for transition metal centers.

For alkenes, it has been demonstrated that the weakening of the carbon-carbon π-bond can be achieved either by inducing a diradical or a zwitterionic character as evidenced by the twisting from planarity and lengthening of the CC distances in $C_1$ (E. Molins, C. Miravitlies, E. Espinosa, M. Ballester, *J. Rog. Chem.* 67, 7175-7178 (2002)) (twist angle: 55°; d$_{CC}$=1.39 Å) and $C_2$ (A. Forni, R. Destro, *Chem. Eur. J.* 9, 5528-5537 (2003)) (twist angle: 86°; d$_{CC}$=1.47 Å), respectively (see FIG. 1). As noted above, small cyclic allenes have a diradical character, but it comes at a cost of dramatically increasing reactivity, such that these molecules are only transient intermediates. To weaken the π-bonds of allenes, yet avoid destabilization, a polarization approach was adopted. Such a polarization can be accomplished either by a push-pull or a push-push substitution pattern. The former, as in D, would impart a carbene character as shown by the resonance structure D', and favor dimerization (R. W. Saalfrank, H. Maid, *Chem. Commun.* 2005, 5953-5967 (2005), R. W. Saalfrank, *Isr. J. Chem.* 26, 181-190 (1985)). Accordingly, the small cyclic allenes provided herein are prepared with a push-push substitution pattern as in E, which promotes the dicarbanionic resonance form E'.

Bent Allenes

As used herein, the term "C—C—C bent allene" refers to an allene compound (or ligand) in which the allene portion is made up of three carbon atoms and in which the carbon-carbon-carbon bond angle (typically 180° in linear allenes) has been "bent" to an angle of 160° or less. Bending an allene out of a linear configuration is accomplished using substituents that provide a polarization of electrons in the allene. While a single substituent can accomplish a suitable polarization, more typically, a "push-push" of electrons is accomplished with substituents on either end of the allene. When multiple substituents are involved, they can be the same or different and generally provide electron donation to the allene. In this manner, the bent allene becomes a strong ligand having properties of a two- to four-electron donor ligand (a carbodianion-type of ligand).

Generally, the bent allenes of the present invention are represented by Formula I:

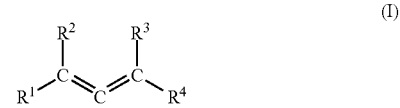

(I)

wherein each of R$^1$, R$^2$, R$^3$ and R$^4$ is independently selected from the group consisting of amino, aryl, heteroaryl, $C_{1-10}$ alkoxy, $C_{2-10}$ alkenyloxy, $C_{2-10}$ alkynyloxy, $C_{1-10}$ alkyl, $C_{3-10}$ cycloalkyl, $C_{2-10}$ alkenyl, $C_{3-10}$ cycloalkenyl, $C_{2-10}$ alkynyl, halogen, aryloxy, heteroaryloxy, $C_{2-10}$ alkoxycarbonyl, $C_{1-10}$ alkylthio, $C_{2-10}$ alkenylthio, $C_{2-10}$ alkynylthio, $C_{1-10}$ alkylsulfonyl, $C_{1-10}$ alkylsulfinyl, aryl-$C_{1-10}$ alkyl, heteroaryl-$C_{1-10}$ alkyl, aryl-$C_{1-10}$ heteroalkyl, heteroaryl-$C_{1-10}$ heteroalkyl, a phosphorus group, a silicon group and a boron group, wherein at least one atom directly adjacent to an allene carbon is selected from the group consisting of N, P, O and S.

Optionally two or four of R$^1$, R$^2$, R$^3$ and R$^4$ are combined to form a 5- to 8-membered carbocyclic or heterocyclic ring.

Additionally, the aliphatic or aromatic portions of R$^1$, R$^2$, R$^3$ and R$^4$ are optionally substituted with from 1 to 4 substituents selected from the group consisting of halogen, cyano, nitro, $C_{1-4}$ alkyl, $C_{2-6}$ alkenyl, $C_{2-6}$ alkynyl, aryl, $C_{1-6}$ alkoxy, $C_{2-6}$ alkenyloxy, $C_{2-6}$ alkynyloxy, aryloxy, $C_{2-6}$ alkoxycarbonyl, $C_{1-6}$ alkylthio, $C_{1-6}$ alkylsulfonyl, $C_{1-6}$ alkylsulfinyl, oxo, imino, thiono, primary amino, carboxyl, $C_{1-6}$ alkylamino, $C_{1-6}$ dialkylamino, amido, nitrogen heterocycles, hydroxy, thiol and phosphorus groups.

In one group of embodiments, the C—C—C bent allene two- to four-electron-donating ligand is a ligand wherein the three allene carbons are ring vertices of a four to eight-membered ring. In particular embodiments, the C—C—C bent allene two- to four-electron-donating ligand has formula I above, wherein $R^1$ is joined with either $R^3$ or $R^4$ to form a five to eight-membered ring (or alternatively, $R^2$ is joined with either of $R^3$ or $R^4$ to form a five to eight-membered ring). In a particularly preferred group of embodiments, the C—C—C bent allene two- to four-electron-donating ligand has the formula,

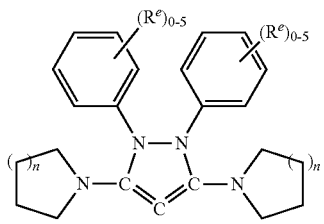

wherein the subscripts n are each independently an integer of from 0 to 4; and each $R^e$ is a substituent independently selected from the group consisting of halogen, cyano, nitro, $C_{1-4}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{2-6}$ alkoxycarbonyl, $C_{1-6}$ alkylthio, $C_{1-6}$ alkylsulfonyl, $C_{1-6}$ alkylsulfinyl, primary amino, carboxyl, $C_{1-6}$ alkylamino, $C_{1-6}$ dialkylamino, amido, hydroxy and thiol groups.

In another group of embodiments, the C—C—C bent allene two- to four-electron-donating ligand is a ligand wherein $R^1$ and $R^2$ are combined to form a ring and $R^3$ and $R^4$ are combined to form a ring. In a particular group of embodiments, the C—C—C bent allene two- to four-electron-donating ligand has the formula:

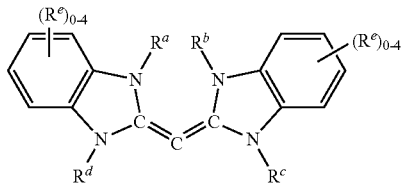

wherein each of $R^a$, $R^b$, $R^c$ and $R^d$ are independently selected from the group consisting of hydrogen, $C_{1-10}$ alkyl, $C_{3-10}$ cycloalkyl, $C_{2-10}$ alkenyl, $C_{3-10}$ cycloalkenyl, $C_{2-10}$ alkynyl, $C_{2-10}$ alkoxycarbonyl, $C_{1-10}$ alkylsulfonyl, $C_{1-10}$ alkylsulfinyl, aryl-$C_{1-4}$ alkyl and heteroaryl-$C_{1-4}$ alkyl; and each $R^e$ is a substituent independently selected from the group consisting of halogen, cyano, nitro, $C_{1-4}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{2-6}$ alkoxycarbonyl, $C_{1-6}$ alkylthio, $C_{1-6}$ alkylsulfonyl, $C_{1-6}$ alkylsulfinyl, primary amino, carboxyl, $C_{1-6}$ alkylamino, $C_{1-6}$ dialkylamino, amido, hydroxy and thiol groups.

Transition Metal Complexes

In another aspect, the present invention provides transition metal complexes useful as catalysts in a variety of synthetic organic reactions. In particular, the catalysts or complexes comprise a transition metal and a bent allene ligand selected from the bent allenes provided above. One of skill in the art will appreciate that such complexes can employ a number of transition metals and have a variety of geometries (e.g., trigonal, square planar, trigonal bipyramidal and the like) depending on the nature of the transition metal and its oxidation state and other factors including, for example, additional ligands.

In general, any metals and transition metals (e.g., a metal having d electrons) can be used to form the complexes/catalysts of the present invention. For example, suitable metals and transition metals are those selected from one of Groups 1-16 of the periodic table or from the lanthanide series. Preferably, the metal will be selected from Groups 5-12 and even more preferably Groups 6-11. For example, suitable metals include silver, gold, molybdenum, platinum, palladium, iron, nickel, iridium, ruthenium and rhodium. The particular form of the metal to be used in the reaction is selected to provide, under the reaction conditions, metal centers which are coordinately unsaturated.

To further illustrate, suitable transition metal complexes and catalysts include soluble or insoluble complexes of silver, gold, molybdenum, platinum, palladium, iron, nickel, iridium, ruthenium and rhodium. Palladium, gold, molybdenum, iridium, ruthenium and nickel are particularly preferred and ruthenium is most preferred.

As noted above, the complexes further comprise a bent allene ligand as described above with respect to formula (I) and formulae (a) and (b). Preferred bent allene ligands are essentially those that have been described as preferred and/or selected embodiments above. The catalyst complex can include additional ligands as required to obtain a stable complex. The additional ligands can be neutral ligands, anionic ligands and/or electron-donating ligands. The ligand can be added to the reaction mixture in the form of a metal complex, or added as a separate reagent relative to the addition of the metal.

Anionic ligands suitable as additional ligands are preferably halide, pseudohalide, tetraphenylborate, perhalogenated tetraphenylborate, tetrahaloborate, hexahalophosphate, hexahaloantimonate, trihalomethanesulfonate, alkoxide, carboxylate, tetrahaloaluminate, tetracarbonylcobaltate, hexahaloferrate(III), tetrahaloferrate(III) or/and tetrahalopalladate(II). Preferably, an anionic ligand is selected from halide, pseudohalide, tetraphenylborate, perfluorinated tetraphenylborate, tetrafluoroborate, hexafluorophosphate, hexafluoroantimonate, trifluoromethanesulfonate, alkoxide, carboxylate, tetrachloroaluminate, tetracarbonylcobaltate, hexafluoroferrate (III), tetrachloroferrate(III) or/and tetrachloropalladate(II). Preferred pseudohalides are cyanide, thiocyanate, cyanate, isocyanate and isothiocyanate. Neutral or electron-donor ligands suitable as additional ligands can be, for example, amines, imines, phosphines, phosphites, carbonyl compounds, alkenyl compounds (e.g., allyl compounds), carboxyl compounds, nitriles, alcohols, ethers, thiols or thioethers. Still other suitable ligands can be carbene ligands such as the diaminocarbene ligands (e.g., NHCs).

While the present invention describes a variety of transition metal complexes useful in catalyzing organic reactions, one of skill in the art will appreciate that many of the complexes can be formed in situ. Accordingly, ligands (either bent allene ligands or additional ligands) can be added to a reaction solution as a separate compound, or can be complexed to the metal center to form a metal-ligand complex prior to its introduction into the reaction solution. The additional ligands are typically compounds added to the reaction solution which can bind to the catalytic metal center. In some preferred embodiments, the additional ligand is a chelating ligand. While the additional ligands can provide stability to the catalytic transition metal complex, they may also suppress unwanted side reactions as well as enhance the rate and efficiency of the desired processes. Still further, in some embodiments, the additional ligands can prevent precipitation of the catalytic transition metal. Although the present invention does not require the formation of a metal-additional ligand complex, such complexes have been shown to be consistent with the postulate that they are intermediates in these reactions and it has been observed the selection of the additional ligand has an affect on the course of the reaction.

In related embodiments, the present invention provides metal complexes, of the type described above, in which the bent allene ligand has a pendent functionalized side chain (e.g., aminoalkyl, mercaptoalkyl, acyloxyalkyl and the like) in which the functional group acts as a ligand to provide a bidentate ligand feature. In still other embodiments, the bent allene ligand forms a metal complex with bidentate ligands that are not tethered to the bent allene moiety.

Reactions Catalyzed by Transition Metal—Bent Allene Complexes

As noted above, the complexes of the present invention are useful in catalyzing a variety of synthetic organic reactions including amine arylation reactions, Suzuki coupling reactions (aryl-aryl or aryl-alkyl coupling reactions), and α-arylation reactions. Still other reactions that can benefit from the above-noted complexes include, for example, hydroformylation (of alkenes and alkynes), hydrosilylation (of alkenes, alkynes, ketones and aldehydes), ring-closing metathesis (RC), ring-opening polymerization metathesis (ROMP), cross metathesis (CM), self metathesis, acyclic diene metathesis polymerization, ene-yne metathesis, carbonylation, hydroarylation and hydroamination.

The reactions of the present invention can be performed under a wide range of conditions, and the solvents and temperature ranges recited herein should not be considered limiting. In general, it is desirable for the reactions to be run using mild conditions which will not adversely affect the reactants, the catalyst, or the product. For example, the reaction temperature influences the speed of the reaction, as well as the stability of the reactants and catalyst. The reactions will typically be run at temperatures in the range of 10° C. to 300° C., more preferably in the range 10° C. to 150° C. For some of the olefin metathesis reactions, a temperature of from 10° C. to 70° C. is preferred. Additionally, the reactions will typically be run for a time period of from 3 minutes to 24 hours, depending on other reaction conditions (e.g., solvent, concentration and amount of catalyst). Typically, the amount of catalyst used will be from 0.2 to 20 mol percent, with 1 to 10 mol percent being preferred.

Additionally, the reactions are generally carried out in a liquid reaction medium, but in some instances can be run without addition of solvent. For those reactions conducted in solvent, an inert solvent is preferred, particularly one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

In some embodiments, reactions utilizing the catalytic complexes of the present invention can be run in a biphasic mixture of solvents, in an emulsion or suspension, or in a lipid vesicle or bilayer. In certain embodiments, the catalyzed reactions can be run in the solid phase with one of the reactants tethered or anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivatization with one or more of substituents of the aryl group.

In view of the above, the present invention provides reaction mixtures as well as methods for conducting certain chemical processes.

Accordingly, the present invention provides reaction mixtures comprising an organometallic complex as described above, a solvent and an olefin substrate, wherein the olefin substrate is selected to participate in an olefin metathesis reaction. In one group of embodiments, the olefin substrate is selected as a substrate for ring closing metathesis. In another group of embodiments, the olefin substrate is selected as a substrate for ring opening polymerization metathesis. In still another group of embodiments, the olefin substrate is selected as a substrate for cross metathesis. In yet another group of embodiments, the olefin substrate is selected as a substrate for acyclic diene polymerization metathesis.

The present invention further provides methods for conducting olefin metathesis, comprising contacting an olefin substrate with an organometallic complex as described above, under metathesis conditions. In one group of embodiments, the olefin substrate is selected as a substrate for ring closing metathesis. In another group of embodiments, the olefin substrate is selected as a substrate for ring opening polymerization metathesis. In still another group of embodiments, the olefin substrate is selected as a substrate for cross metathesis and is combined with a second olefin substrate, generally a tri-substituted olefin or a di-substituted olefin having additional substitution at an allylic position. In yet another group of embodiments, the olefin substrate is selected as a substrate for acyclic diene polymerization metathesis. As noted above, the amount of the organometallic complex will typically be from 0.2 to 20 mol percent (relative to the olefin substrate or substrates), with 1 to 10 mol percent being preferred.

Preparation of Bent Allenes and Complexes

Among the possible synthetic routes to cyclic allenes, deprotonation of the conjugate acid was chosen. A major advantage of deprotonation is its rapidity, even at low temperatures, so that species that are only moderately stable can still be characterized. Therefore, the readily available, thermally and air stable, 3,5-diaminopyrazolium salts 1 (A. I. Eid, M. A. Kira, H. H. Fahmy, *J. Pharm. Belg.* 33, 303-311 (1978)) represented logical precursors for five-membered cyclic allenes featuring four π-donating amino groups. Monitoring the reaction of 1a with n-butyllithium at −78° C. by NMR spectroscopy revealed a clean deprotonation as shown by the disappearance of the CH proton signal, and indicated a symmetrical product 2a (FIG. 1). This compound is stable at room temperature, and after workup was isolated as orange crystals in 26% yield. According to an X-ray diffraction study, derivative 2a is the desired cyclic allene, as a lithium tetrafluoroborate adduct. In contrast with the perpendicular pairs of substituents found in classical allenes, the four nitrogen centers and the C1C2C3 fragment of 2a are nearly in the same plane (maximum deviation: 0.0653 Å). Based on the case of the free bis(diisopropylamino)cyclopropenylidene (V. Lavallo, Y. Canac, B. Donnadieu, W. W. Schoeller, G. Bertrand, *Science* 312, 722-724 (2006)), and its lithium salt adducts (V. Lavallo, Y. Ishida, B. Donnadieu, G. Bertrand, *Angew. Chem. Int. Ed.* 45, 6652-6655 (2006)), it is safe to predict that the geometric parameters of 2a will be close to those of the corresponding salt free allene. The CC bond lengths (1.398-1.403 Å) are much longer than the standard allene value (1.31 Å) (F. H. Allen, O. Kennard, D. G. Watson, L. Brammer, G. Orpen, R. Taylor, *J. Chem. Soc. Perkin Trans. II* 1987, S1-S19 (1987)), and the C1C2C3 fragment is far from linear, the angle reaching 100.8°. Interestingly, compound 2a exists in the solid state as a racemic mixture, due to the trans relationship of the phenyl groups. This indicates that the endocyclic nitrogen atoms are in a pyramidal environment (sum of the angles: 337.7° and 335.9°), and consequently that their lone pairs do not interact with the allene π-system. Since only the nearly planar exocyclic amino substituents (sum of the angles: 355.0° and 357.2°) are used to polarize the p-bonds, and these substituents are not bulky, this implies that a variety of cyclic bent allenes are accessible.

Interestingly, the relative position of the $^{13}$C NMR signals for the central and terminal carbon nuclei of the CCC framework of 2a (114.4 and 176.3 ppm, respectively) is opposite to that observed for non-polarized allenes (185-215 and 60-130 ppm, respectively) (22), but similar to that reported for tetrakis(dimethylamino)allene 3 (136 and 162 ppm) (R. W. Saalfrank, C.-J. Lurz, in *Houben Weyl*, H. Kropf, E. Schaumann, Eds., (Georg Thieme Verlag, Stuttgart, 1993), Vol. E15, pp 2959-3107). The striking similarities observed in the NMR data for 2a and 3 prompted us to investigate the geometry of acyclic tetra(amino)substituted allenes. During the preparation of this manuscript, Tonner and Frenking (R. Tonner, G. Frenking, G. *Angew. Chem. Int. Ed.* 46, 8695-8698 (2007)) published a detailed computational investigation of a compound that is similar to 6, and that they described as a strongly basic compound composed of "a divalent carbon(0) with two N-heterocyclic carbene ligands". The predicted equilibrium geometry (CCC bond angle of 131.8° and CC distances of 1.358 Å) is very close to that observed experimentally for 6. In order to maximize the pushing effects, and in the hope of obtaining a crystalline material (3 is a liquid), we chose allene 6 as a target. Indeed, we have already shown that the inclusion of the amino groups into a ring favors the conjugation of the lone pairs with the adjacent CC π-bond (V. Lavallo, Y. Canac, B. Connadieu, W. W. Schoeller, G. Bertrand, *Angew. Chem. Int. Ed.* 45, 3488-3491 (2006)); moreover, the benzannulation should promote crystallinity.

Figure 2:
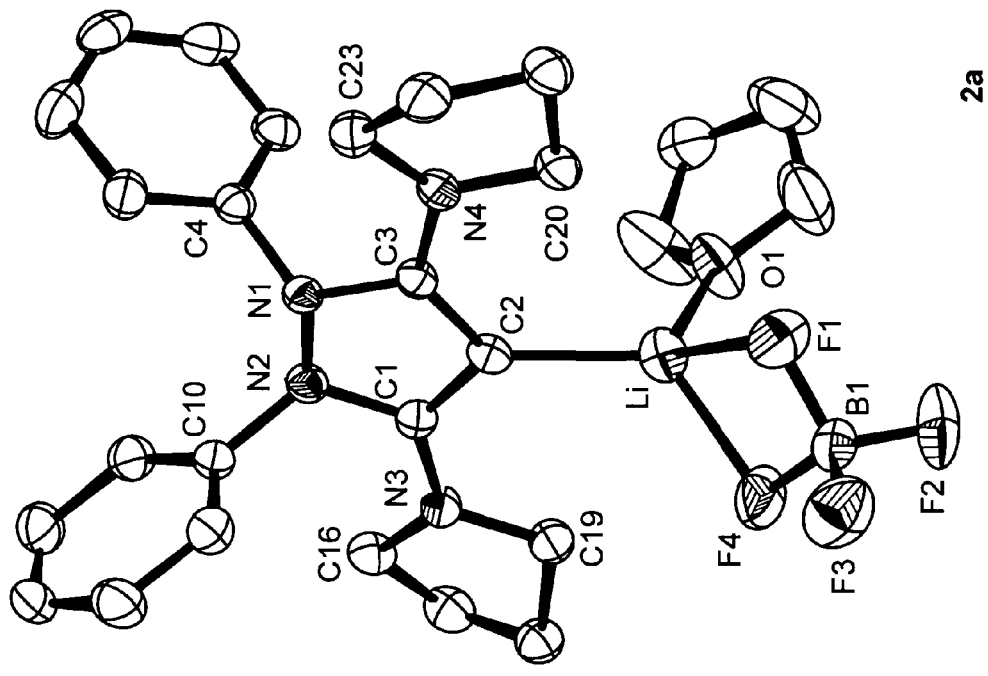
FIG. 2 illustrates the synthesis of cyclic allene-lithium salt adducts 2, and solid-state structure of one of the enantiomers of 2a·2 THF (for clarity, H atoms and a non-coordinated THF molecule are omitted). C1-C2, 1.403±2 Å; C2-C3, 1.398±2 Å; C3-N1, 1.408±2 Å; N1-N2, 1.444±2 Å; C1-N2, 1.411±2 Å; C1-N3, 1.349±2 Å; C2-Li, 2.106±3 Å; C3-N4, 1.353±2 Å; C1-C2-C3, 100.8±1°; C1-C2-Li, 129.5±1°; C3-C2-Li, 129.2±2°; C2-C3-N4, 128.3±2°; C2-C3-N1, 114.7±1°; N1-C3-N4, 117.0±1°; C3-N1-N2, 104.9±1°; C3-N1-C4, 121.0±N2-N1-C4, 111.9±1°; N1-N2-C10, 109.6±1°; N1-N2-C1, 104.2±1°; C1-N2-C1, 122.0±1°; C2-C1-N3, 127.3±2°, C2-C1-N2, 114.8±1°; N2-C1-N3, 117.9±1°; C1-N3-C16, 125.5±1°; C1-N3-C19, 120.2±1°; C19-N3-C16, 111.6±1°; C3-N4-C23, 123.7±1°; C3-N4-C20, 120.7±1°; C20-N4-C23, 111.61±1°.
Figure 2:
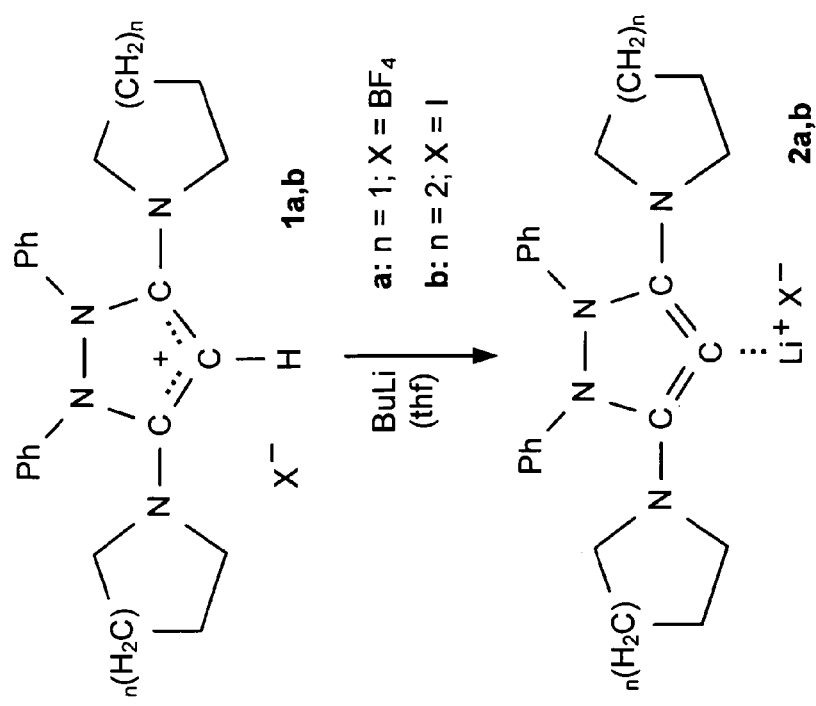

Allene 6 was synthesized in two steps from the readily prepared bis(N-methylbenzimidazol-2-yl)methane 4 (FIG. 2) (S. Elgafi, L. D. Field, B. A. Messerle, P. Turner, T. W. Hambley, *J. Organomet. Chem.* 588, 69-77 (1999)). Bis-alkylation of 4 with excess methyl trifluoromethanesulfonate in acetonitrile gave rise to the dicationic salt 5 in 50% isolated yield. Subsequent bis-deprotonation using potassium hexamethyldisilazane afforded allene 6, which was isolated as yellow crystals in 32% yield. Because of the poor solubility of 6 at room temperature, $^{13}$C NMR characterization was performed at 50° C. in $d_6$-benzene. The chemical shifts of the central and terminal allenic carbons (110.2 and 144.8 ppm, respectively) are in the range observed for 2a and 3. A single crystal X-ray diffraction study revealed that the four amino groups do in fact cause a dramatic effect on the geometry of allene 6. Although the bond lengths are only slightly longer (C1-C2=1.343 Å) than the standard C=C bond length of an allene, the two NC1N planes are not perpendicular but twisted by 69°. Most strikingly, the allene framework is severely bent with a C2-C1-C2' angle of 134.8° ! Clearly the allene π-system has been totally broken, and the central carbon atom is not sp-hybridized as in typical all-carbon allenes; this is confirmed by the free rotation around the CC bonds, at room temperature, revealed by NMR spectroscopy (only one signal for the four Me groups). Although extremely water sensitive, allene 6 is indefinitely stable at room temperature both in solution and in the solid state [m.p. 150-152° C.].

Just like bent allenes, carbenes have been considered for a long time as reactive intermediates (R. A. Moss, M. S. Platz, M. Jones Jr., Eds., *Reactive Intermediate Chemistry* (Wiley: New York, 2004). With the availability of stable versions, carbenes have become ubiquitous ligands for transition metals. Importantly, because of the presence of a lone pair and a partially filled p-orbital, carbenes are strong σ-donor and weak π-acceptor ligands, which often lead to highly active catalyst (F. Glorius, Ed., N-Heterocyclic Carbenes in *Transition Metal Catalysis* (*Topics in Organometallic Chemistry*) (Springer-Verlag: New York, 2006), S. P. Nolan, Ed., *N-Heterocyclic Carbenes in Synthesis* (Wiley-VCH: New York, 2006). Interestingly, the dicarbanionic resonance form E' suggests that bent allenes 2 and 6 should be stronger σ-donors than carbenes and also strong π-donors.

Figure 3:
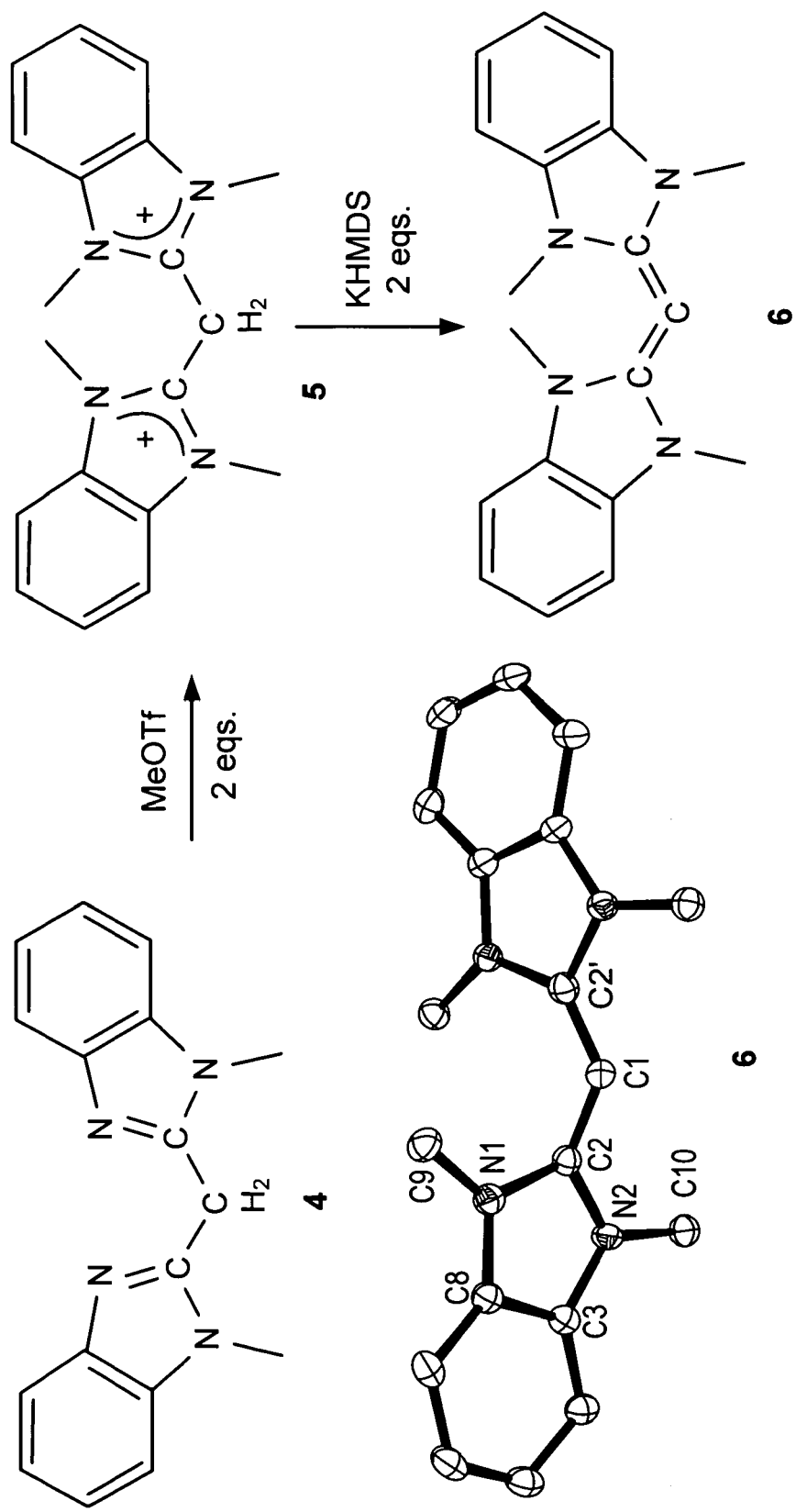
FIG. 3 illustrates the synthesis of acyclic bent allene 6, and solid-state structure of one of the enantiomers (for clarity, H atoms are omitted). C1-C2, 1.343±2 Å; C2-N2, 1.400±2 Å; C2-N1, 1.407±2 Å; C2-C1-C2', 134.8±2°; C1-C2-N1, 129.7±1°; C1-C2-N2, 125.8±1°; N1-C2-N2, 104.1±1°; C2-N1-C9, 124.3±1°; C8-N1-C9, 124.5±1°; C8-N1-C2, 110.6±1°; C2-N2-C10, 123.7±1°; C2-N2-C3, 111.1±1°; C3-N2-C10, 125.1±1°.
Figure 4:
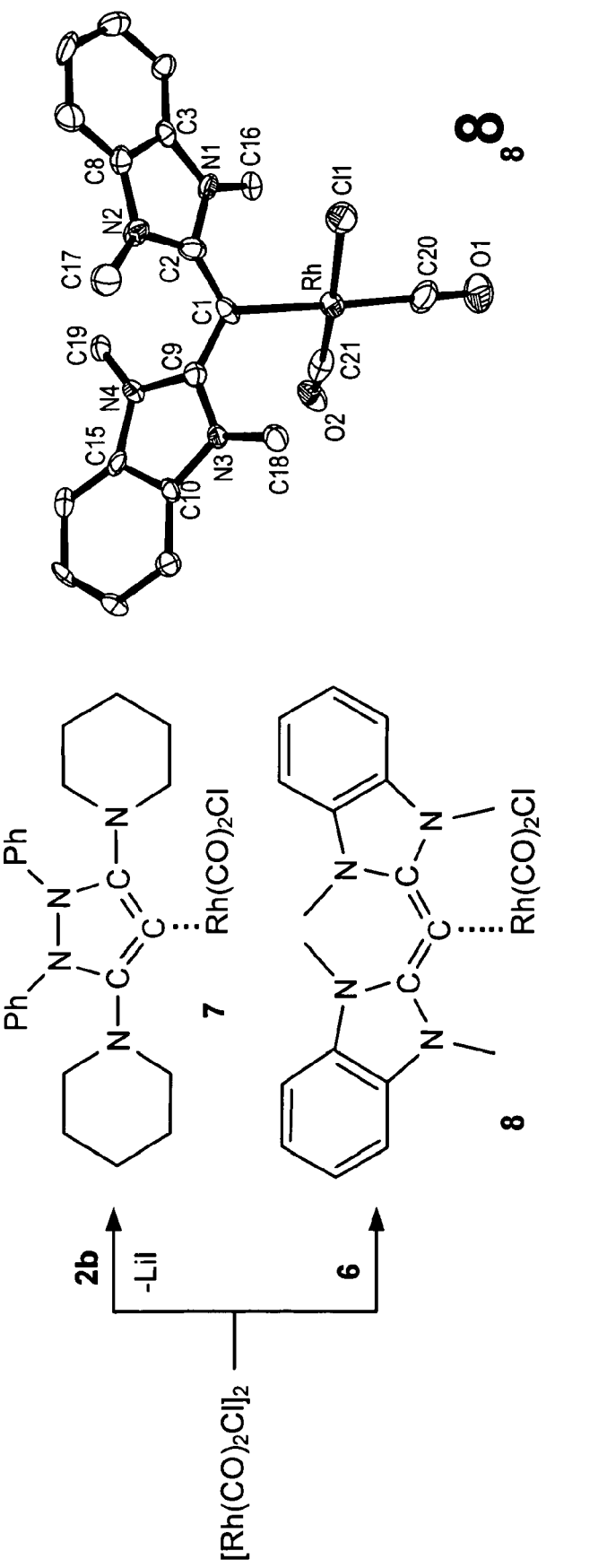
FIG. 4 illustrates the synthesis of allene rhodium complexes 7 and 8, and solid-state structure of one of the enantiomers of 8 (for clarity, H atoms are omitted). C1-C2, 1.398±10 Å; C1-Rh, 2.416±3 Å; C2-N1, 1.419±9 Å; C2-N2, 1.351±9 Å; C2-C1-C9, 121.2±7°; C9-C1-Rh, 121.3±5°; C2-C1-Rh, 117.4±5°; C1-C2-N2, 126.3±7°; C1-C2-N1, 127.9±7°; N1-C2-N2, 105.5±6°.
Figure 5:
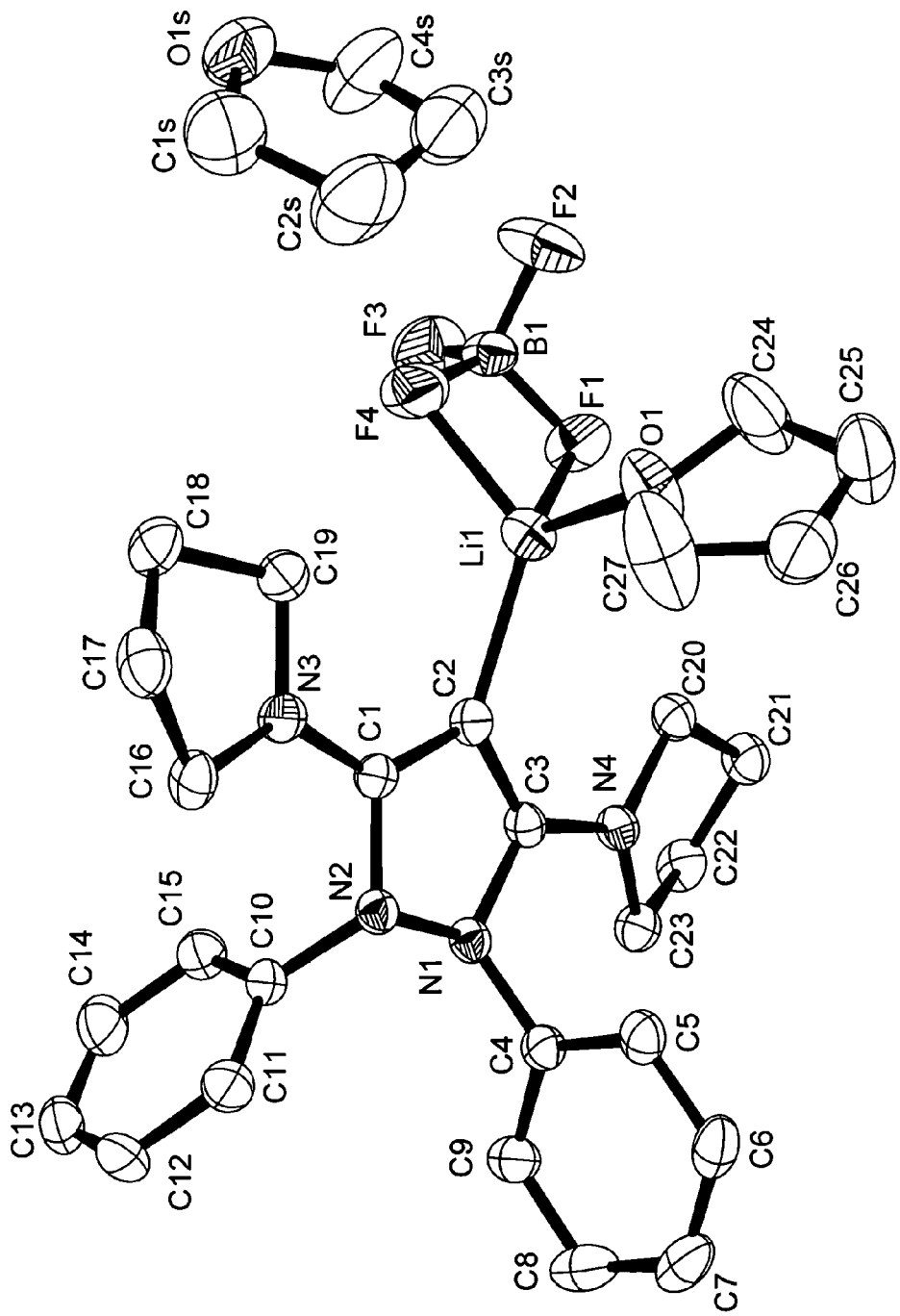
FIGS. 5-7 provide ORTEP views of 2a 2THF, 6 and 8.
Figure 6:
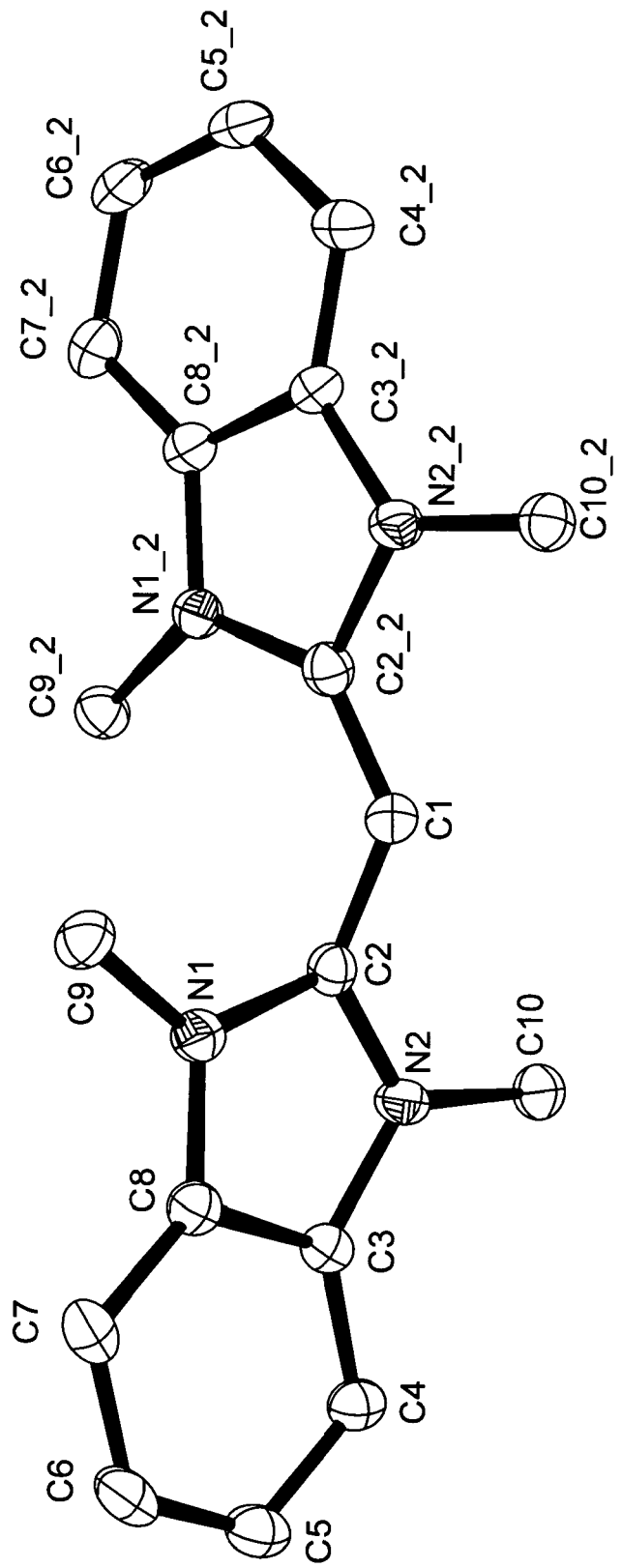
Figure 7:
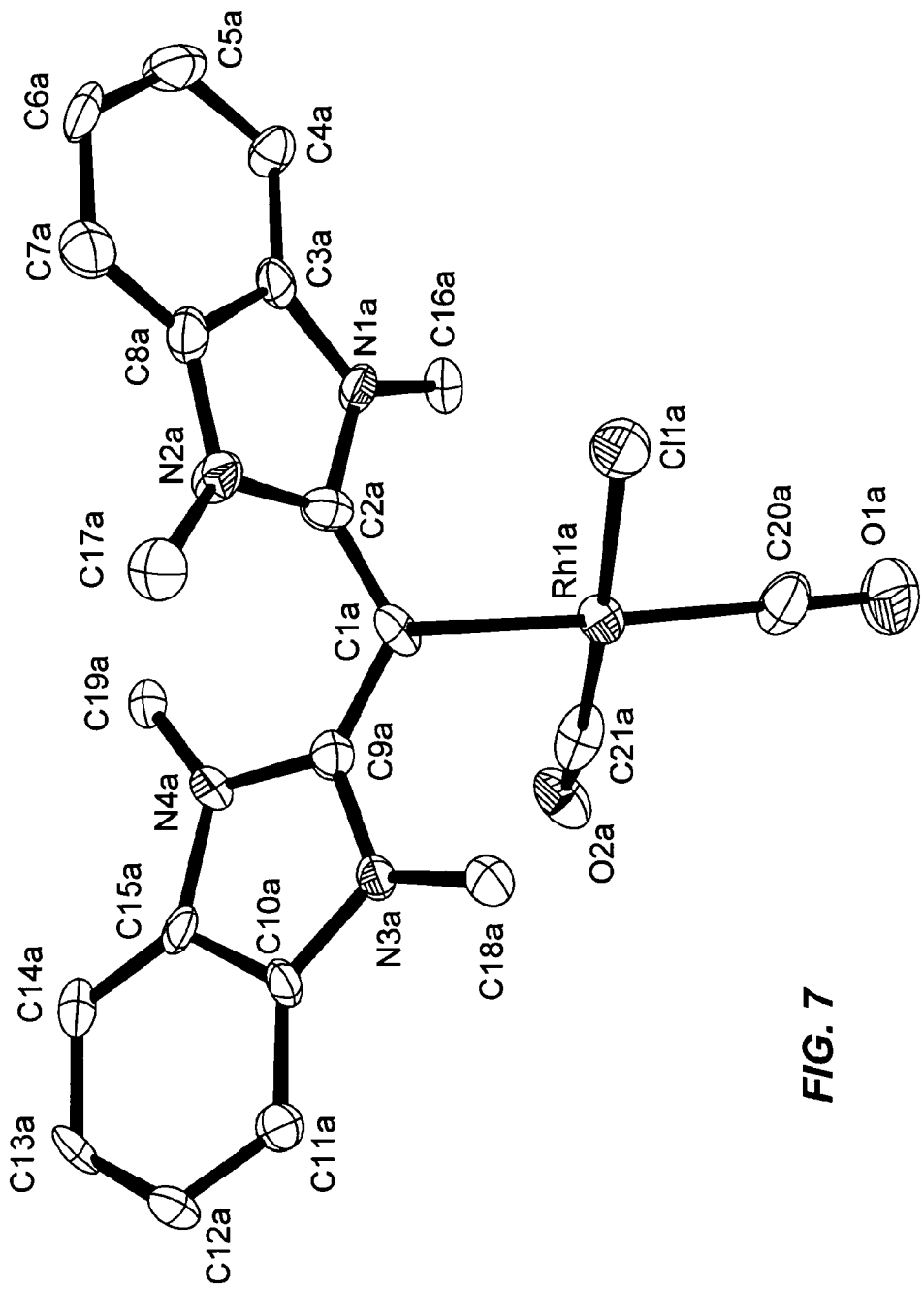

The carbonyl stretching frequencies of cis-[RhCl(CO)$_2$(L)] complexes are recognized as an excellent measure of the electronic properties of the ligand L (A. Fürstner, M. Alcarazo, H. Krause, C. W. Lehmann, *J. Am. Chem. Soc.* 129, 12676-12677 (2007), A. R. Chianese, X. W. Li, M. C. Janzen, J. W. Faller, R. H. Crabtree, *Organometallics* 22, 1663-1667 (2003), G. D. Frey, W. W. Schoeller, *Organometallics*, in press). Bent allene complexes 7 and 8 were readily prepared in 95 and 56% yield by addition of half an equivalent of [RhCl(CO)$_2$]$_2$ to 2b and 6, respectively (FIG. 3). As expected, the average value of the carbonyl stretching frequencies for complexes 7 (2016 cm$^{-1}$) and 8 (2014 cm$^{-1}$) are significantly lower than those observed for analogous complexes featuring a five-membered N-heterocyclic carbene (2058-2036 cm$^{-1}$), or even the strongly basic bis(diisopropylamino)carbene (2020 cm$^{-1}$) (G. D. Frey, W. W. Schoeller, *Organometallics*, in press).

Usually, the bonding in compounds of the first long-row elements serves as a model for developing and understanding the chemistry of their heavier congeners. The results reported here demonstrate that, in the same way, the bonding in heavier main group elements can be a source of inspiration for new bonding situations in classical organic molecules. By analogy with the recent developments in carbene chemistry, the allenes described herein will find applications as strong donor ligands for transition metals.

EXAMPLES

Synthesis and Spectroscopic Data

All experiments were carried out under dry argon using standard Schlenk or dry box techniques. Solvents were dried by standard methods and distilled under argon. $^1$H (300 MHz) and $^{13}$C-NMR (75 MHz) spectra were recorded on a Bruker 300 spectrometer at a temperature of 25° C. unless otherwise indicated, and referenced to the residual $^1$H, and $^{13}$C signals of the solvents. NMR multiplicities are abbreviated as follows: s=singlet, d=doublet, m=multiplet, br=broad signal. Coupling constants J are given in Hz. Infrared spectra were recorded in $CH_2Cl_2$ using a Bruker Equinox 55 or IFS120 HR. Melting points were measured with a Büchi melting point apparatus system.

Example 1

2a: To a suspension of 1a (A. I. Eid, M. A. Kira, H. H. Fahmy, *J. Pharm. Belg.* 33, 303-311 (1978).) (1.0 g, 2.24 mmol) in THF (50 mL) at −78° was added n-BuLi (2.5 M, 0.9 mL, 2.24 mmol). The mixture was stirred for 15 minutes and then removed from the cold bath. When the reaction reached R.T. the solvent was concentrated to 50% of the volume and diethyl ether (20 mL) was added. After storing the solution at −20° overnight, orange crystals of 2a, suitable for an X-ray diffraction study, were collected (0.308 g). Yield 26.2%; Mp. 130-132° C. (dec.); $^1$H NMR ($C_6D_6$): δ 1.28 (br m, 8 H), 1.45 (br m, 4 H), 3.31 (br m, 8 H), 3.62 (br m, 4 H), 6.95-7.05 (br m, 10 H); $^{13}$C NMR ($C_6D_6$): δ 26.0 ($CH_2$), 26.1 ($CH_2$), 51.2 ($NCH_2$), 68.3 ($OCH_2$), 114.4 (CCC), 127.9 (CH arom.), 128.2 (CH arom.), 129.3 (CH arom.), 144.7 (C arom.), 176.3 (NCN).

2b: 1b was deprotonated in an analogous fashion to that of 2a, except that the reaction mixture was concentrated to dryness without crystallization. Alternatively, the deprotonation can be carried out in benzene at R.T., with lithium diisopropylamide. The crude NMR spectra of the latter method are typically greater than 90% pure after a 40 minute reaction time, contaminated only by 1b. Mp 128-130° C. (dec.); $^1$H NMR ($C_6D_6$): δ 1.18 (br m, 4 H), 1.23 (br m, 8 H), 3.58 (br m, 8 H), 6.80-7.05 (br m, 10H); $^{13}$C NMR ($C_6D_6$): δ 24.6 ($CH_2$), 26.2 ($CH_2$), 52.0 ($NCH_2$), 118.6 (CCC), 127.9 (CH arom.), 128.2 (CH arom.), 130.0 (CH arom.), 145.5 (C arom.), 180.2 (NCN).

5: MeOTf (4.0 mL, 35.3 mmol) was added dropwise to a stirred mixture of 4 (S. Elgafi, L. D. Field, B. A. Messerle, P. Turner, T. W. Hambley, *J. Organomet. Chem.* 588, 69-77 (1999). (3.0 g, 10.9 mmol) in dry acetonitrile (30 mL). After 1.5 hours at room temperature, ether (60 mL) was slowly added to the stirred mixture to afford a golden yellow crystalline precipitate. Filtration, washing with ether (2×25 mL) and drying under vacuum afforded 6.05 g of crude 5. The crude solid was dissolved in hot acetonitrile (40 mL), then dichloromethane (60 mL) was added and the mixture was left to cool overnight. Filtration, washing with dichloromethane (5×12 mL) and drying under vacuum afforded 5 as a white solid. Yield: 3.30 g (5.46 mmol) 50%; Mp. 246-250° C.; $^1$H NMR ($CD_3CN$): δ 3.97 (s, 12 H), 5.44 (s, 2 H), 7.85 (AA'BB' system, 8 H); $^{13}$C NMR ($CD_3CN$): δ 22.9 ($CH_2$), 34.2 ($NCH_3$), 114.8 (CH arom), 129.1 (CH arom.), 133.5 (C arom.), 144.7 (NCN).

6: A slurry of potassium hexamethyldisilazane (0.73 g, 3.66 mmol) in benzene (12 mL) was added dropwise at room temperature to a suspension of 5 (1.0 g, 1.65 mmol) in benzene (4 mL). After stirring for 35 minutes the mixture was heated to boiling and rapidly filtered. After the solution was cooled to room temperature for 30 minutes, crystalline yellow precipitate of 6 was collected by filtration, washed with ether (3×15 mL) and dried under vacuum (yield 0.087 g). The benzene filtrate was added to the original precipitate and again heated to boiling and rapidly filtered. Volatiles were removed under vacuum and the residue was washed with ether (3×15 mL) and dried. The resulting solid was then recrystallized from boiling tetrahydrofuran (2 mL), washed with tetrahydrofuran (2×1 mL), and dried under vacuum to afford 6 (0.073 g) as yellow crystals suitable for an X-ray diffraction study. Total yield 0.160 g (0.526 mmol) 32%; Mp. 150-152° C. (dec.); $^1$H NMR ($C_6D_6$): δ 2.89 (s, 12 H), 6.47 (m, 4 H), 6.93 (m, 4 H); $^{13}$C NMR ($C_6D_6$, 50° C.): δ 29.7 ($NCH_3$), 105.2 (CH arom), 110.2 (CCC), 135.9 (C arom.), 144.8 (NCN).

7. A shlenk flask was loaded with 2b (0.250 g, 0.48 mmol) and $[Rh(CO)_2Cl]_2$ (0.093 g, 0.24 mmol) followed by addition of benzene (5 mL). The reaction mixture was stirred for one hour and subsequently filtered to remove LiI. The resulting solution was concentrated to dryness to afford 7. Yield 0.266 g (0.456 mmol) 95%; Mp 185-187° C. (dec.); $^1$H NMR ($C_6D_6$): δ 0.90-1.23 (br m, 12 H), 3.65 (br m, 8 H), 6.80-7.00 (br m, 10 H); $^{13}$C NMR ($C_6D_6$): δ 23.7 ($CH_2$), 25.4 ($CH_2$), 52.9 ($NCH_2$), 99.1 (d, $^1J_{CRh}$=30.4 Hz, CRh), 127.5 (CH arom.), 129.8 (CH arom.), 130.2 (CH arom.), 143.9 (C arom.), 174.4 (NCN), 185.3 (d, $^1J_{CRh}$=80.1 Hz, RhCO), 189.4 (d, $^1J_{CRh}$=53.4 Hz, RhCO); IR ($CH_2Cl_2$, cm$^{-1}$): 2052, 1979.

8: A suspension of 6 (0.060 g, 0.197 mmol) in benzene (3 mL) was added dropwise to a solution $[Rh(CO)_2Cl]_2$ (0.038 g, 0.098 mmol) in benzene (4 mL), immediately giving a red mixture. The orange precipitate was isolated by filtration. Yield: 0.055 g (0.110 mmol) 56%; Mp. 205-210° C. (dec.); $^1$H NMR ($CDCl_3$): δ 3.62 (s, 12 H), 7.07 (m, 8 H), 7.18 (m, 8 H); $^{13}$C NMR ($CDCl_3$): δ 33.2 ($NCH_3$), 64.1 (d, $^1J_{CRh}$=27.1 Hz, CRh), 108.3 (CH arom.), 122.4 (CH arom.), 133.5 (C arom.), 159.0 (NCN), 185.5 (d, $^1J_{CRh}$=56.8 Hz, RhCO), 185.3 (d, $^1J_{CRh}$=78.4 Hz, RhCO); IR ($CH_2Cl_2$, cm$^I$): 2052, 1976.

Single crystals, suitable for X-ray diffraction, were grown by from a 1:1 benzene:tetrahydrofuran solution.

Crystal Structure Determination of Compounds 2a, 6 and 8

The Bruker X8-APEX (Bruker (2005). APEX 2 version 2.0-2. Bruker AXS Inc., Madison, Wis., U.S.A.) X-ray diffraction instrument with Mo-radiation was used for data collection of compounds 2a, 6 and 8. All data frames were collected at low temperature (T=100 K) using an a), cp-scan mode and integrated using a Bruker SAINTPLUS software package. (Bruker (2005). SAINT version V7.21A. Bruker AXS Inc., Madison, Wis., USA). The intensity data were corrected for Lorentzian polarization. Absorption corrections were performed using the SADABS program. (Bruker (2004). SADABS version 2004/1. Bruker Analytical X-Ray System, Inc., Madison, Wis., USA). The SIR97 software package (A. Altomare, M. C. Burla, M. Camalli, G. L. Cascarano, C. Giacovazzo, A. Guagliardi, A. G. G. Moliterni, G. Polidori, R. Spagna, SIR 97, *J. Appl. Cryst.* 32, 115 (1999)) was used for direct methods of phase determination, and Bruker SHELXTL software package (Bruker (2003). SHELXTL Software Version 6.14, December, Bruker Analytical X-Ray System, Inc., Madison, Wis., USA) was used for structure refinement and difference Fourier maps. Atomic coordinates, isotropic and anisotropic displacement parameters of all the non-hydrogen atoms of two compounds were refined by means of a full matrix least-squares procedure on $F^2$. All H-atoms were included in the refinement in calculated positions riding on the C atoms, with U[iso] fixed at 20% higher than isotropic parameters of carbons atoms to which they were attached. Drawings of molecules were performed using ORTEP 3 (L. J. Farrugia, ORTEP-3 for Windows, *J. Appl. Cryst.* 30, 565 (1997)) with thermal ellipsoids at the 50% probability level.

What is claimed is:

1. An organometallic complex comprising a metal atom selected from groups 1-16 of the periodic table and a C—C—C bent allene two- to four-electron-donating ligand having the formula:

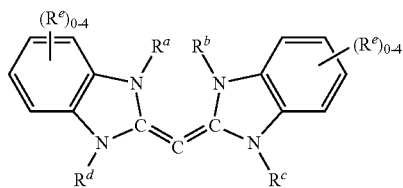

wherein each of $R^a$, $R^b$, $R^c$ and $R^d$ are independently selected from the group consisting of hydrogen, $C_{1-10}$ alkyl, $C_{3-10}$ cycloalkyl, $C_{2-10}$ alkenyl, $C_{3-10}$ cycloalkenyl, $C_{2-10}$ alkynyl, $C_{2-10}$ alkoxycarbonyl, $C_{1-10}$ alkylsulfonyl, $C_{1-10}$ alkylsulfinyl, aryl-$C_{1-4}$ alkyl and heteroaryl-$C_{1-4}$ alkyl; and each $R^e$ is a substituent independently selected from the group consisting of halogen, cyano, nitro, $C_{1-4}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{2-6}$alkoxycarbonyl, $C_{1-6}$ alkylthio, $C_{1-6}$ alkylsulfonyl, $C_{1-6}$ alkylsulfinyl, primary amino, carboxyl, $C_{1-6}$ alkylamino, $C_{1-6}$ dialkylamino, amido, hydroxy and thiol groups.

2. An organometallic complex comprising a metal atom selected from groups 1-16 of the periodic table and a C—C—C bent allene two- to four-electron-donating ligand having the formula:

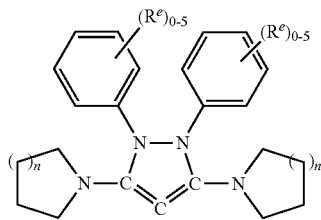

wherein the subscripts n are each independently an integer of from 0 to 4; and
  each $R^e$ is a substituent independently selected from the group consisting of halogen, cyano, nitro, $C_{1-4}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{2-6}$ alkoxycarbonyl, $C_{1-6}$ alkylthio, $C_{1-6}$ alkylsulfonyl, $C_{1-6}$ alkylsulfinyl, primary amino, carboxyl, $C_{1-6}$ alkylamino, $C_{1-6}$ dialkylamino, amido, hydroxy and thiol groups.

3. A reaction mixture comprising an organometallic complex of claim 1, a solvent and an olefin substrate, wherein said olefin substrate is selected to participate in an olefin metathesis reaction.

4. A reaction mixture of claim 3, wherein said olefin substrate is selected as a substrate for ring closing metathesis.

5. A reaction mixture of claim 3, wherein said olefin substrate is selected as a substrate for ring opening polymerization metathesis.

6. A reaction mixture of claim 3, wherein said olefin substrate is selected as a substrate for cross metathesis.

7. A reaction mixture of claim 3, wherein said olefin substrate is selected as a substrate for acyclic diene polymerization metathesis.

8. A method for conducting olefin metathesis, comprising contacting an olefin substrate with an organometallic complex of claim 1, under metathesis conditions.

9. A method of claim 8, wherein said olefin substrate is selected as a substrate for ring closing metathesis.

10. A method of claim 8, wherein said olefin substrate is selected as a substrate for ring opening polymerization metathesis.

11. A method of claim 8, wherein said olefin substrate is selected as a substrate for cross metathesis.

12. A method of claim 8, wherein said olefin substrate is selected as a substrate for acyclic diene polymerization metathesis.

13. A reaction mixture comprising an organometallic complex of claim 2, a solvent and an olefin substrate, wherein said olefin substrate is selected to participate in an olefin metathesis reaction.

14. A reaction mixture of claim 13, wherein said olefin substrate is selected as a substrate for ring closing metathesis.

15. A reaction mixture of claim 13, wherein said olefin substrate is selected as a substrate for ring opening polymerization metathesis.

16. A reaction mixture of claim 13, wherein said olefin substrate is selected as a substrate for cross metathesis.

17. A reaction mixture of claim 13, wherein said olefin substrate is selected as a substrate for acyclic diene polymerization metathesis.

18. A method for conducting olefin metathesis, comprising contacting an olefin substrate with an organometallic complex of claim 2, under metathesis conditions.

19. A method of claim 18, wherein said olefin substrate is selected as a substrate for ring closing metathesis.

20. A method of claim 18, wherein said olefin substrate is selected as a substrate for ring opening polymerization metathesis.

21. A method of claim 18, wherein said olefin substrate is selected as a substrate for cross metathesis.

22. A method of claim 18, wherein said olefin substrate is selected as a substrate for acyclic diene polymerization metathesis.

23. An organometallic complex of claim 1, wherein said metal atom is selected from the group consisting of silver, gold, molybdenum, platinum, palladium, iron, nickel, iridium, ruthenium and rhodium.

24. An organometallic complex of claim 2, wherein said metal atom is selected from the group consisting of silver, gold, molybdenum, platinum, palladium, iron, nickel, iridium, ruthenium and rhodium.

* * * * *